United States Patent [19]

Kotani et al.

[11] Patent Number: 4,808,466

[45] Date of Patent: Feb. 28, 1989

[54] DEODORANT SHEET

[75] Inventors: Motoharu Kotani; Shinzo Ishikawa, both of Himeji; Keishi Sato, Suita, all of Japan

[73] Assignee: Daicel Chemical Industries, Ltd., Sakai, Japan

[21] Appl. No.: 84,144

[22] Filed: Aug. 12, 1987

[30] Foreign Application Priority Data

Oct. 9, 1986 [JP] Japan ................................ 61-240999

[51] Int. Cl.$^4$ ........................... B32B 7/00; B32B 9/00
[52] U.S. Cl. ..................................... 428/254; 428/260; 428/284; 428/286; 428/304.4; 428/905; 428/907; 428/913

[58] Field of Search ............... 428/304.4, 305.5, 317.9, 428/905, 907, 254, 260, 284, 286, 913

[56] References Cited

U.S. PATENT DOCUMENTS

| | | | |
|---|---|---|---|
| 3,567,118 | 3/1971 | Shepherd et al. | 428/905 |
| 3,755,064 | 8/1973 | Maerson | 428/905 |
| 4,504,541 | 3/1985 | Yasuda et al. | 428/264 |

*Primary Examiner*—William J. Van Balen
*Attorney, Agent, or Firm*—Birch, Stewart, Kolasch & Birch

[57] ABSTRACT

A deodorant sheet effectively comprises a porous base sheet having a coating layer provided thereon the coating layer comprising a resin, a deodorant and a biological activity-inhibiting substance.

13 Claims, No Drawings

DEODORANT SHEET

BACKGROUND OF THE INVENTION

1. Field of the Invention

The present invention relates to a deodorant sheet which has both a deodorant effect and antibiotic activities such as antibacterial, antimold and vermin-proof activities that are fast to washing, and which can, therefore, be used for multiple purposes in the daily environment.

2. Description of the Prior Art

Deodorants are classified into adsorptive type ones and reactive type ones according to the mechanism thereof. A divalent iron compound which is a reactive type deodorant, particularly ferrous sulfate, has a strong deodorant effect for malodorous components originating from ammonia, amine, and the like. Thus, it is used as a deodorant by being carried on a carrier such as an activated carbon or zeolite. Further, it is incorporated into various daily necessaries such as calendars, posters, and wallpaper. Thus, daily necessaries having a deodorant effect, for example, a deodorant calendar, may be marketed.

The deodorant activity of ferrous sulfate is so strong that it is quickly reacted with ammonia even when it is carried on a cloth by impregnating the cloth therewith. However, it is oxidized with oxygen in the air to develop a yellowish brown color and it has a tendency to decrease its deodorant capacity. Therefore, the application of its deodorant capacity to a material having a long service period has been difficult. An increase in an amount of ferrous sulfate for the purpose of enhancing the deodorant effect of such a material leads to a serious influence of coloring.

Since ferrous sulfate is soluble in water, ferrous sulfate carried on a cloth is readily removed when washed with water, resulting in the loss of the desired deodorant effect. And what is worse, the yellowish brown color itself which is formed cannot be readily removed. Accordingly, the application of ferrous sulfate to clothing and bedding has been difficult.

Further it is found that, where a sheet material is a porous material compatible with a film-forming substance, incorporation of a ferrous sulfate monohydrate powder into the film forming substance can advantageously provide a deodorant sheet material free of any change in appearance with time. Moreover, the sheet has a persistent deodorant capacity and a fastness to washing with water or cleaning when the chain film-forming substance is resistant to water. This is disclosed in Japanese patent publication A No. 62-64538, which is after the priority date of the application.

SUMMARY OF THE INVENTION

In the invention, the subject matter described in the above named Japanese patent publication No. 62-64538 is applied to a porous sheet material such as paper, woven fabric and non-woven fabric. If biological activity-inhibiting functions such as vermin-proof, antibacterial and antimold functions can be simultaneously imparted, they will be further useful.

As a result of an examination of the effect of the combined use of ferrous sulfate monohydrate powder with a biological activity-inhibiting substance such as a vermin-proof agent, an antibacterial agent and an antimold agent, the inventors of the present invention have found that the effect of the biological activity-inhibiting substance is not lost by the addition of ferrous sulfate monohydrate. The reason for this has not been elucidated in detail but is believed that it has something to do with the fact that the deodorant reaction of ferrous sulfate monohydrate is mainly based on neutralization, while its oxidation and reduction reactivities are low.

The inventors of the present invention have also found that basic zinc carbonate is effective for a wider range of malodorous gases than ferrous sulfate monohydrate and does not deteriorate the effect of biological activity-inhibiting substances. Hence, basic zinc carbonate is a deodorant suitable for the object of the presnt invention.

The present invention has been made based on the foregoing findings, and relates to a deodorant sheet comprising a porous sheet base material having a coating resin layer formed thereon, the coating layer containing both a deodorant and a biological activity-inhibiting substance.

A deodorant sheet of the invention comprises a porous base sheet having a coating layer provided thereon, the coating layer comprising a resin, a deodorant and a biological activity-inhibiting substance.

It is preferable that the coating layer comprises 1 to 30 g per 1 $m^2$ of the deodorant, 0.03 to 1 g per 1 $m^2$ of the biological activity-inhibiting substance and the resin in an amount of 1 to 5 times as much as the total weight of the deodorant and the biological activity-inhibiting substance.

The porous sheet base material to be used in the present invention is mainly a sheet material made of a fibrous material such as paper, woven fabric or non-woven fabric but may be also a porous film or a foamed plastic sheet.

Deodorants suitable for the present invention include salts of polyvalent metals such as iron, copper, zinc, manganese, and aluminum. Those having a relatively low solubility in water or those insoluble in water are preferred. Particularly, basic zinc carbonate and ferrous sulfate monohydrate are suitable.

The biological activity-inhibiting substance suitable for the present invention is in the form of fine particles, insoluble in water, relatively high in heat stability and relatively low in toxicity. Particularly useful examples thereof include anti-fungal agents such as N-(fluorodichloromethylthio)phthalimide and N,N-dimethyl-N'-phenyl-N'-(fluorodichloromethylthio)sulfamide.

The coating resin layer suitable for the present invention is desirably one formed from a water-insoluble film-forming substance. Examples of such a substance include olefin copolymers, acrylic resins, and synthetic rubbers.

The term "coating resin layer on the porous base material, is intended to extensively refer to those integrally constituting a product together with the porous base material and involves, for example, a back size of a carpet, a flocking binder of a flocked cloth, an adhesive binder of a laminated woven fabric, a constituent binder of a non-woven fabric, and adhesive layer of a wallpaper, a surface finish resin of a woven fabric, a non-woven fabric or a knitted product, and a vehicle of pigment printing.

The coating resin layer is formed by coating, spraying, or impregnating the porous base material with a mixture of a solution of a coating resin, preferably an organic solvent solution, an aqueous emulsion, or a melt in the case of a low-melting resin with finely powdered deodorant and biological activity-inhibiting substance, followed by drying and cooling. The biological activity-inhibiting substance such as an antibacterial agent, an antimold agent and a vermin-proof agent may be dissolved in the above-mentioned solution, emulsion or melt, or mixed therewith in the form of fine powder.

Where basic zinc carbonate is used as a deodorant, no particular problems are involved in using a mixture of finely powdered basic zinc carbonate with a coating resin solution or emulsion since basic zinc carbonate is insoluble in water and commonly used organic solvents. On the other hand, ferrous sulfate monohydrate is soluble in hot water, and shows a tendency to flocculate in an emulsion when it is dissolved in water. Therefore, ferrous sulfate monohydrate may be used with a solution of a coating resin. When the coating resin is in the form of emulsion, alternatively ferrous sulfate monohydrate is mixed with the emulsion at a low of a temperature as possible at which the solubility is low, for example, at 15° C. or lower, and applied to a sheet base material soon thereafter.

Even when a large amount of a deodorant and a biological activity-inhibiting substance are contained in the coating layer, the deodorant sheet of the present invention can exhibit a practically sufficient effect if the coating layer is relatively thin and the surface area is large. When the coating resin laye is insoluble in water, a sheet having good fastness to washing as to deodorant and biological activity-inhibiting effects can be obtained. Where the deodorant and the biological activity-inhibiting substance are insoluble in water, the fastness to washing as to the above-mentioned effects is further enhanced.

The deodorant sheet of the present invention can be widely utilized as an underlay of a wardrobe, an underlay of a closet, an underlay of a straw an underlay of a closet, an underlay of a tatami-mat, socks and an insole of shoes, various base sheet, a bedding, and a diaper cover. There are many articles not requiring a fastness to washing depending on the use thereof. Even in those articles, there occurs no ooze of a deodorant and a biological activity-inhibiting substance when wetted with water, so that the effects advantageously last.

DETAILED DESCRIPTION OF PREFERRED EMBODIMENTS

The following Examples will further illustrate the present invention, but they should not be construed as limiting the scope of the invention.

EXAMPLE 1

There were used basic zinc carbonate or ferrous sulfate monohydrate powder (passing through a 30-mesh sieve) as the deodorant, an N-(fluorodichloromethylthio)phthalimide powder as the antimold and antibacterial agent, a woven fabric made of a polyester staple fiber (plain weave, areal weight: 50 g/m$^2$) as the porous sheet material, and an acrylic copolymer emulsion (Cevian A-4659, manufactured by Daicel Chemical Industries, Ltd., solid content: 40%) as the coating resin. The following procedure was undertaken.

The deodorant and the antibacterial/antimold agent were dispersed each in about ten-fold as much water, and admixed with the acrylic emulsion so that the solid content ratio of the deodorant:the antibacterial/antimold agent:acrylic emulsion was 36:4:60.

The resulting mixture was applied to the polyester woven fabric by padding at a weight ratio of about 1:1, followed by air drying at 140° C. Thus, an acrylic resin-coated cloth was obtained. The amount of the fixed acrylic resin in the treated cloth was 9 g/m$^2$, while that of the fixed deodorant was 5 g/m2 and that of the fixed antibacterial/antimold agent was 0.5 g/m2.

The deodorant and antibacterial properties of the treated cloth were measured by the following methods.

Ammonia gas (NH$_3$): 0.4 g (size: 11 cm×18 cm) of the non-woven fabric was placed in a 6.3-1 desiccator wherein the initial ammonia gas concentration (C$_0$) was preliminarily adjusted to 85 to 105 ppm. The ammonia gas concentration (C) after 4 hours was measured to calculate a C/C$_0$ ratio.

Hydrogen sulfide gas (H$_2$S): 0.4 g (size: 11 cm×18 cm) of the non-woven fabric was placed in a 6.5-1 desiccator wherein the initial hydrogen sulfide gas concentration (C$_0$) was preliminarily adjusted to 30 to 40 ppm. The hydrogen sulfide gas concentration (C) after 4 hours was measured to calculate a C/C$_0$ ratio.

Antibaceterial properties: The test was conducted using Staphylococcus aureus in accordance with the ATCC test method 100-1981. A cloth of 3 cm×3 cm was used as the test specimen. The experiment was repeated three times and the results were shown using an average value. The test cloth was placed in an Erlenmeyer flask and sterilized. Thereafter, 0.3 ml of a test bacterium solution containing about 10$^5$ bacteria/ml was dropped and uniformly inoculated. Thereafter, the bacteria were cultured at room temperature for 6 hours. After completion of culture, living bacteria in the test specimen were dispersed in a liquid by using a sterilized physiological saline containing 0.1% Triton X-100. The dispersion was diluted and placed in a Petri dish. A plate was prepared from a Tryptone-D agar and culture was conducted at 35° C. for 48 hours. After completion of culture, the number of colonies appearing in the Petri dish was counted and the rate of a decrease in bacteria relative to the number of living bacteria separately counted just after inoculation was determined.

The measurement was conducted as regards a treated cloth and a cloth obtained by washing a treated cloth under the following conditions, followed by washing with water and drying.

Washing test: conditions of washing with an electric machine

Detergent: neutral detergent 10 g/5 l (water)
Washing time: 5 minutes
Dehydration time: 1 minute
Washing in clean water: 8 minutes
Dehydration time: 2 minutes The test results are shown together with those of Comparative Example 1 in Table 1.

COMPARATIVE EXAMPLE 1

The treatment was conducted using a deodorant and antibacterial antimold agent capable of being directly applied from an aqueous solution instead of those used in Example without using a coating resin. Specifically, ferrous sulfate heptahydrate as the deodorant and N-methylpyrrolidone as the antibacterial/antimoldy agent were used each in the form of a 20% aqueous solution. The aqueous solutions were sprayed over a polyester non-woven fabric and dried so that the deodorant solid content was 5 g/m2 and the antifungal/antimoldy agent content was 0.5 g/m2.

The results of the tests conducted in the same manner as in Example are shown in Table 1.

TABLE 1

| | Deodorant | Number of times of washing | Deodorant capacity (C/C$_0$) ammonia | Deodorant capacity (C/C$_0$) hydrogen sulfide | Antifungal activity |
|---|---|---|---|---|---|
| Non-treated fabric | — | 0 | 0.50 | 0.95 | 0 |
| Ex. 1 | ferrous sulfate | 0 | 0.01 | 0.84 | 99.9 |
| | | 10 | 0.40 | 0.90 | 95.3 |
| | | 20 | 0.50 | 0.95 | 90.0 |
| | | 30 | 0.50 | 0.95 | 78.5 |
| | zinc carbonate | 0 | 0.10 | 0.00 | 99.9 |
| | | 10 | 0.25 | 0.20 | 96.8 |
| | | 20 | 0.32 | 0.20 | 97.5 |
| | | 30 | 0.35 | 0.22 | 85.4 |
| Comp. Ex. 1 | ferrous sulfate | 0 | 0.01 | 0.84 | 99.9 |
| | | 1 | 0.47 | 0.95 | 0 |
| | | 2 | 0.50 | 0.95 | 0 |

What is claimed is:

1. A deodorant sheet, which comprises, a porous base sheet having a coating layer provided thereon, wherein the coating layer comprises 1 to 30 g per 1 m$^2$ of a deodorant, 0.03 to 1 g per 1 m$^2$ of a biological activity-inhibiting substance and a resin in an amount of 1 to 5 times as much as the total weight of the deodorant and the biological activity-inhibiting substance.

2. The deodorant sheet as claimed in claim 1, wherein the resin is film-forming and water-insoluble.

3. The deodorant sheet as claimed in claim 1, wherein the deodorant is a multi-valent salt of iron, copper, zinc, manganese or aluminum.

4. The deodorant sheet as claimed in claim 1, wherein the deodorant is a basic zinc carbonate or ferrous sulfate monohydrate in the form of fine powder.

5. The deodorant sheet as claimed in claim 1, wherein the porous base sheet is a fibrous material, a porous film or a foamed plastic sheet.

6. The deodorant sheet as claimed in claim 1, wherein the biological activity-inhibiting substance is in the form of fine particles, insoluble in water, relatively high in heat stability and relatively low in toxicity.

7. The deodorant sheet as claimed in claim 1, wherein the biological activity-inhibiting substance is selected from at least one member of the group consisting of an antibacterial agent, an antimold agent and a verminproof agent.

8. The deodorant sheet as claimed in claim 1, wherein the biological activity-inhibiting substance is an antifungal agent selected from the group consisting of N-(fluorodichloromethylthio)-phthalimide and N,N-dimethyl-N'-phenyl-N'-(fluorodichloromethylthio)sulfamide.

9. The deodorant sheet as claimed in claim 1, wherein the resin is selected from the group consisting of olefin copolymers, acrylic resins, and synthetic rubbers.

10. The deodorant sheet as claimed in claim 1, wherein the deodorant is a basic zinc carbonate or a ferrous sulfate monohydrate powder, the antimold and the antibacterial agent is an N-(fluorodichloro-methylthio)-phthalimide powder, the porous sheet material is a woven fabric made of a polyester staple fiber, and the coating resin is an acrylic copolymer emulsion.

11. The deodorant sheet as claimed in claim 1, wherein the deodorant is adsorptive and reactive.

12. The deodorant sheet as claimed in claim 1, wherein the coating layer contains a uniform blend of resin, deodorant and biological activity-inhibiting substance.

13. A deodorant sheet which comprises a porous base sheet having a coating layer provided thereon, wherein the coating layer comprises 1 to 30 per 1 m$^2$ of a deodorant, 0.03 to 1 g per 1 m$^2$ of a biological activity-inhibiting substance and a resin in an amount of 1 to 5 times as much as the total weight of the deodorant and the biological activity-inhibiting substance and wherein the deodorant is adsorptive and reactive and the coating layer contains a uniform blend of resin, deodorant and biological activity-inhibiting substance.

* * * * *